United States Patent
Goldfain et al.

(10) Patent No.: US 10,078,226 B2
(45) Date of Patent: Sep. 18, 2018

(54) PORTABLE EYE VIEWING DEVICE ENABLED FOR ENHANCED FIELD OF VIEW

(71) Applicant: Welch Allyn, Inc., Skaneateles Falls, NY (US)

(72) Inventors: Ervin Goldfain, Syracuse, NY (US); Raymond A. Lia, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 14/334,196

(22) Filed: Jul. 17, 2014

(65) Prior Publication Data
US 2015/0103317 A1  Apr. 16, 2015

Related U.S. Application Data

(60) Provisional application No. 61/890,618, filed on Oct. 14, 2013.

(51) Int. Cl.
*A61B 3/13* (2006.01)
*G02B 27/10* (2006.01)
(Continued)

(52) U.S. Cl.
CPC .......... *G02B 27/10* (2013.01); *A61B 3/10* (2013.01); *A61B 3/1208* (2013.01); *A61B 3/14* (2013.01);
(Continued)

(58) Field of Classification Search
CPC .......... A61B 3/1233; A61B 3/14; A61B 3/10; A61B 3/1208; A61B 3/156; G02B 27/10; G02B 15/10; G02B 27/106; G02B 27/14
See application file for complete search history.

(56) References Cited

U.S. PATENT DOCUMENTS 2,902,911 A * 9/1959 Noyori ............... A61B 3/14
                                                        351/206
3,586,424 A    6/1971 Schenk et al.
(Continued)

FOREIGN PATENT DOCUMENTS

DE   197 44 131 A1   4/1998
EP   1 152 687 B1    9/2004
(Continued)

OTHER PUBLICATIONS

Kimme et al. "Optimized flash light-emitting diode spectra for mobile phone cameras," Applied Optics vol. 52, No. 36, pp. 8779-8788, 2013.*
(Continued)

*Primary Examiner* — Jordan Schwartz
*Assistant Examiner* — George G King

(57) ABSTRACT

An ophthalmoscope includes an illumination assembly having a light source disposed along an illumination axis and an imaging assembly configured for delivering an image to an imaging device. Each of the imaging and illumination assemblies are disposed in an instrument housing, the ophthalmoscope being configured for attachment to an electronic imaging device and in which the imaging assembly produces a field of view of about 40 degrees to permit more comprehensive eye examinations to be reliably conducted. In at least one version, a portable electronic device, such as a smart device, can be coupled to the instrument or configured to wirelessly receive images therefrom.

9 Claims, 13 Drawing Sheets

(51) Int. Cl.
  *A61B 3/15* (2006.01)
  *A61B 3/10* (2006.01)
  *A61B 3/12* (2006.01)
  *A61B 3/14* (2006.01)
  *G02B 15/10* (2006.01)
  *G02B 27/14* (2006.01)

(52) U.S. Cl.
  CPC .............. *A61B 3/156* (2013.01); *G02B 15/10* (2013.01); *G02B 27/106* (2013.01); *G02B 27/14* (2013.01)

(56) References Cited

U.S. PATENT DOCUMENTS

| | | | |
|---|---|---|---|
| 3,614,214 A | 10/1971 | Cornsweet et al. | |
| 3,638,641 A | 2/1972 | Abromavage et al. | |
| 3,698,099 A | 10/1972 | Matsura | |
| 3,698,387 A | 10/1972 | Moore et al. | |
| 3,840,004 A | 10/1974 | Heine | |
| 3,893,447 A | 7/1975 | Hochheimer et al. | |
| 3,914,032 A | 10/1975 | Takano et al. | |
| 4,132,466 A | 1/1979 | Matsumura | |
| 4,252,420 A | 2/1981 | Kohayakawa | |
| 4,265,518 A | 5/1981 | Matsumura | |
| 4,365,872 A * | 12/1982 | Nunokawa | A61B 3/156 351/208 |
| 4,366,811 A | 1/1983 | Riester | |
| 4,442,736 A | 12/1983 | Nunokawa | |
| 4,439,024 A | 3/1984 | Ito | |
| 4,564,273 A | 1/1986 | Iba et al. | |
| 4,567,881 A | 2/1986 | Heller | |
| 4,662,360 A | 5/1987 | O'Hara et al. | |
| 4,679,919 A | 7/1987 | Itch et al. | |
| 4,682,866 A | 7/1987 | Volk | |
| 4,721,378 A | 1/1988 | Volk | |
| 4,785,796 A | 11/1988 | Mattson | |
| 4,856,872 A | 8/1989 | Spitznas et al. | |
| 4,997,419 A | 3/1991 | Lakatos et al. | |
| 5,070,883 A | 12/1991 | Kasahara | |
| 5,093,719 A | 3/1992 | Prescott | |
| 5,255,025 A | 10/1993 | Volk | |
| 5,363,839 A | 11/1994 | Lankford | |
| 5,390,663 A | 2/1995 | Schaefer | |
| 5,424,789 A | 6/1995 | Volk | |
| 5,579,063 A | 11/1996 | Magnante et al. | |
| 5,624,453 A | 4/1997 | Ahmed | |
| 5,658,235 A | 8/1997 | Priest et al. | |
| 5,713,047 A | 1/1998 | Kohayakawa | |
| 5,720,756 A | 2/1998 | Green et al. | |
| 5,722,762 A | 3/1998 | Soll | |
| 5,751,395 A | 5/1998 | Thall | |
| 5,795,067 A | 8/1998 | Fraden et al. | |
| 5,842,971 A | 12/1998 | Yoon | |
| 5,880,813 A | 3/1999 | Thall | |
| 5,919,130 A | 7/1999 | Monroe et al. | |
| 5,982,555 A | 11/1999 | Melville et al. | |
| 6,019,721 A | 2/2000 | Holmes et al. | |
| 6,053,875 A | 4/2000 | Rosenbaum et al. | |
| 6,099,537 A | 8/2000 | Sugai et al. | |
| 6,106,457 A | 8/2000 | Perkins et al. | |
| 6,129,661 A | 10/2000 | Iafrati et al. | |
| 6,142,934 A | 11/2000 | Lagerway et al. | |
| 6,190,310 B1 | 2/2001 | Cook | |
| 6,213,938 B1 | 4/2001 | Cook | |
| 6,254,271 B1 | 7/2001 | Lin | |
| 6,296,358 B1 * | 10/2001 | Cornsweet | A61B 3/156 351/206 |
| 6,331,156 B1 | 12/2001 | Haefele et al. | |
| 6,383,133 B1 | 5/2002 | Jones | |
| 6,425,857 B1 | 7/2002 | Rudischhauser et al. | |
| 6,450,970 B1 | 9/2002 | Mahler et al. | |
| 6,475,138 B1 | 11/2002 | Schechter et al. | |
| 6,511,420 B1 | 1/2003 | Farrell et al. | |
| 6,537,208 B1 | 3/2003 | Konno | |
| 6,554,765 B1 | 4/2003 | Yarush et al. | |
| 6,692,431 B2 | 2/2004 | Kazakevich | |
| 7,029,439 B2 | 4/2006 | Roberts et al. | |
| 7,048,379 B2 | 5/2006 | Miller et al. | |
| 7,177,088 B2 | 2/2007 | Hirata | |
| 7,224,822 B2 | 5/2007 | Heacock | |
| 7,290,882 B2 | 11/2007 | Collins et al. | |
| 7,399,275 B2 | 7/2008 | Goldfain et al. | |
| 7,448,753 B1 | 11/2008 | Chinnock | |
| 7,553,020 B2 | 6/2009 | Goldfain et al. | |
| 7,597,443 B2 | 10/2009 | Fujii et al. | |
| 7,677,730 B2 | 3/2010 | Shimizu | |
| D613,402 S | 4/2010 | Roberts et al. | |
| 7,762,950 B2 | 7/2010 | Hirata | |
| 7,803,110 B2 | 9/2010 | Goldfain et al. | |
| 7,854,510 B2 | 12/2010 | Verdooner et al. | |
| 7,901,353 B2 | 3/2011 | Vayser | |
| 8,000,022 B2 | 8/2011 | Niederer | |
| 8,043,211 B2 | 10/2011 | Hirata | |
| 8,100,826 B2 | 1/2012 | MacKinnon et al. | |
| 8,109,981 B2 | 2/2012 | Gertner et al. | |
| 8,152,718 B2 | 4/2012 | Cheng | |
| 8,159,153 B2 | 4/2012 | Hunn | |
| D659,840 S | 5/2012 | Cheng et al. | |
| 8,210,680 B2 | 7/2012 | Tanguay, Jr. et al. | |
| 8,231,522 B2 | 7/2012 | Endo et al. | |
| 8,245,935 B2 | 8/2012 | Vinogradov | |
| 8,469,882 B2 | 6/2013 | Andreassen et al. | |
| 2001/0014112 A1 | 8/2001 | Yamaka | |
| 2002/0085616 A1 | 7/2002 | Yu | |
| 2002/0097379 A1 * | 7/2002 | Goldfain | A61B 3/158 351/221 |
| 2002/0143239 A1 | 10/2002 | Henzler | |
| 2002/0188177 A1 | 12/2002 | Miyanaga | |
| 2002/0193665 A1 | 12/2002 | Jones | |
| 2003/0063386 A1 | 4/2003 | Slawson et al. | |
| 2003/0187331 A1 | 10/2003 | Faludi et al. | |
| 2004/0174498 A1 | 9/2004 | Zorn et al. | |
| 2004/0263784 A1 * | 12/2004 | Cornsweet | A61B 3/12 351/221 |
| 2005/0027168 A1 | 2/2005 | Strom et al. | |
| 2005/0027169 A1 | 2/2005 | Goldfain et al. | |
| 2005/0043588 A1 | 2/2005 | Tsai | |
| 2005/0043591 A1 | 2/2005 | Witte | |
| 2006/0020176 A1 | 1/2006 | Berall | |
| 2006/0159155 A1 | 7/2006 | Lantz et al. | |
| 2006/0183977 A1 | 8/2006 | Takakazu | |
| 2006/0227415 A1 | 10/2006 | Caldwell et al. | |
| 2007/0030573 A1 | 2/2007 | Batchko et al. | |
| 2007/0255108 A1 | 11/2007 | Schmitz | |
| 2008/0051637 A1 | 2/2008 | Andreassen et al. | |
| 2008/0079897 A1 | 4/2008 | Goldfain et al. | |
| 2009/0251792 A1 | 10/2009 | Suzuki et al. | |
| 2011/0013297 A1 | 1/2011 | Barnes et al. | |
| 2011/0060184 A1 | 3/2011 | Rothberg et al. | |
| 2011/0085138 A1 | 4/2011 | Filar | |
| 2011/0116040 A1 | 5/2011 | Biernat et al. | |
| 2011/0176221 A1 | 7/2011 | Tanaka et al. | |
| 2011/0234977 A1 | 9/2011 | Verdooner | |
| 2012/0143004 A1 | 6/2012 | Gupta et al. | |
| 2012/0229617 A1 | 9/2012 | Yates et al. | |
| 2013/0057828 A1 | 3/2013 | De Smet | |
| 2013/0083183 A1 | 4/2013 | Cheng et al. | |
| 2013/0083185 A1 * | 4/2013 | Coleman, III | A61B 3/14 348/78 |
| 2013/0114148 A1 | 5/2013 | Aschwanden et al. | |
| 2013/0128223 A1 * | 5/2013 | Wood | A61B 1/0019 351/206 |

FOREIGN PATENT DOCUMENTS

| | | |
|---|---|---|
| EP | 1 138 255 A1 | 10/2011 |
| TW | 201216916 A1 | 5/2012 |
| TW | 201229557 A1 | 7/2012 |
| WO | WO 99/42760 | 8/1999 |
| WO | WO 02/056756 A2 | 7/2002 |
| WO | WO 2005/053519 A1 | 6/2005 |
| WO | WO 2007/026158 A1 | 3/2007 |

(56) References Cited

FOREIGN PATENT DOCUMENTS

| WO | 2011042722 A1 | 4/2011 |
|---|---|---|
| WO | WO 2011/047214 A2 | 4/2011 |
| WO | WO 2011/050496 A1 | 5/2011 |
| WO | 2012082696 A1 | 6/2012 |
| WO | WO 2013/071153 A1 | 5/2013 |

OTHER PUBLICATIONS

Hecht, Optics, Second Edition, p. 149, 1987.*

Dreher, Andreas W., Field Portable Digital Ophthalmoscope/Fundus Camera, Laser Diagnostic Technologies, Inc., San Diego, CA, Jun. 1997 (26 pages).

Non-Paraxial Design for a Transportable Digital Retinal Imager, Frontiers in Optics, Rochester, NY, Oct. 12, 2004, http://www.opticsinfobase.org/abstract.cfm?uri=FiO-2004-FWM5.

Optomap Panoramic200, http://www.joneseyecenters.com/index.cfm/technology/optomap, Date Accessed Feb. 27, 2013.

International Search Report and Written Opinion for PCT/US2014/056570, dated Jan. 5, 2015 (12 pages).

Zoom lens design using liquid lens for laparosocpe; Seungwan Lee et al.; Optics Express, vol. 21, Issue 2, pp. 1751-1761; © 2013; 11 pages.

Implementing both short-and long-working-distance optical trappings into a commercial microscope; Pavel Kraikivski et al., Journal: Review of Scientific Instruments, vol. 77, No. 11, p. 113703; © Nov. 2006; 10 pages.

4-bit digital liquid lens for variable focal length; Dong Woo Lee et al.; Transducer 2009; pp. 2306-2309; © 2009; 4 pages.

Liquid lens: An advancement in optical communications; Shawn Patrick Casey; Journal of Automation, Mobile Robotics & Intelligent Systems, vol. 1, No. 2, pp. 67-70; © Jun. 2007; 4 pages.

Australian Patent Examination Report for AU 2012335072; dated May 24, 2016; 2 pages.

Australian Government, IP Australia, Examiner's First Report on Patent Application No. 2001263366 by Welch Allyn, Inc.; dated Dec. 9, 2004; 2 pages.

Australian Government, IP Australia, Examiner's Second Report on Patent Application No. 2001263366 by Welch Allyn, Inc.; dated Dec. 19, 2005; 2 pages.

Japanese Patent Office; Examiners Mailing No. 036153, Notice of Grounds for Rejection; dated Jan. 31, 2006 for Japanese Patent Application No. 2000-583418; 3 pages.

International Search Report and Written Opinion of the International Searching Authority for International Application No. PCT/US2007/065367; dated Jun. 3, 2008; 11 pages.

International Search Report; PCT/US2008/073956; dated Mar. 10, 2009; 2 pages.

European Search Report for EP Application No. 08798437.3; dated Oct. 27, 2010; 7 pages.

Medimaging Integrated Solution Inc., http://www.miis.com.tw?option=product&language=zh-tw&mod=5, accessed Apr. 18, 2013; 11 pages.

Digital Hand-held Diagnostic Set, Medimaging Integrated Solution, Inc.; 3 pages.

Rudolf Riester GmbH—medical diagnostic instruments; Source: http://www.riester.de/Home.1+B6Jkw9MSZMPTA_.0.html, date accessed: Sep. 14, 2012; 2 pages.

Parnes, et al. (1996); Advances in the Development of the Interferometric Otoscope; Laryngoscope, 106; pp. 263-267; 5 pages.

Nishikawa, et al. (2011); A Novel Colonoscope with High Color-Rendering White Light-Emitting Diodes; vol. 73, No. 3; pp. 598-602; www.giejournal.org; 5 pages.

International Search Report and Written Opinion of the International Searching Authority for International Application No. PCT/US2012/064510; dated Apr. 29, 2013; 17 pages.

Rajewski (2012; An Optical Engineering Feat from the Kitchen, Cummings School of Veterinary Medicine at Tufts University; 2 pages.

All-N1 Video Otoscopy (MD Scope); Source: http://www.iedmed.com/products/all-n1-video-otoscopy; date accessed: Oct. 25, 2011; 2 pages.

* cited by examiner

PORTABLE EYE VIEWING DEVICE ENABLED FOR ENHANCED FIELD OF VIEW

CROSS REFERENCE TO RELATED APPLICATIONS

This application claims priority pursuant to relevant portions of 35 U.S.C. § 119 to provisional application U.S. Ser. No. 61/890,618, filed Oct. 14, 2013, the entire contents of which are herein incorporated by reference.

TECHNICAL FIELD

The application is generally related to the field of diagnostic medicine. More specifically, the application is directed to a hand-held or bench top ophthalmic device having an optical assembly that provides an enhanced field of view of the eye of a patient and enables enhanced diagnostic eye examinations, such as diabetic retinopathy, to be reliably performed. Real time images that are captured by the ophthalmic device can be directed to a portable electronic device, such as a smartphone, which can be integrated with the instrument to receive images or be remotely connected therewith.

BACKGROUND OF THE PRIOR ART

Ophthalmoscopes are commonly known medical diagnostic instruments used to perform routine examinations of the eye of a patient during a primary physician's visit. Due to their relatively low cost, these instruments are commonly found in the physician's office, hospitals and urgent care medical facilities. A typical ophthalmoscope is defined by an instrument head that is attached to the upper end of a handle portion, enabling the instrument to be relatively compact and capable of being held for use in a single hand of the caregiver. The handle portion retains a source of power (e.g., a plurality of rechargeable batteries) for energizing a contained light source, such as an incandescent lamp or at least one LED, in order to provide sufficient light to the intended target (i.e., the eye), through a distal end of the instrument head. An optical or imaging system contained within the instrument head images the illuminated retina of the eye and directs that image to either an eyepiece or an electronic imaging element, which is disposed at the proximal end of the instrument head.

Fundus cameras, such as described by EP 1 138 255 A1, are a much more sophisticated diagnostic apparatus, as compared to ophthalmoscopes, that are also used for measuring and determining various conditions involving the eye. These latter devices are quite prohibitive in cost, as compared to typical ophthalmoscopes, and can often easily exceed $25,000. The optical systems incorporated in fundus cameras are considerably more intricate and complex than those used in ophthalmoscopes and are also much larger, typically requiring a patient to utilize a chin rest or similar configuration for purposes of stability when conducting an examination. Advantageously, these instruments are configured to provide a field of view of at least 30 to 40 degrees relative to a target of interest (i.e., the eye), which adds significant functionality and capability as compared to direct ophthalmoscopes, the latter usually having a more restricted field of view of only about 5 degrees. Having a larger field of view is essential for enabling more comprehensive diagnoses, such as diabetic retinopathy, to be reliably conducted. Diabetic retinopathy often has no early warning signs, but first stages can be detected by fundus photography in which microaneurysms (microscopic blood-filled bulges in the artery walls), as well as retinal ischemia (blocked or narrowing retinal blood vessels) indicative of the lack of blood flow can be readily and proactively detected.

Given the present state of healthcare reform, a general need exists to provide an eye viewing device, such as an ophthalmoscope, that can reliably provide a larger field of view in order to permit more comprehensive eye examinations to be conducted, but in lieu of a fundus camera.

To that end, there have been numerous attempts to design diagnostic instruments that enable a caregiver to view more of the fundus of the eye. The majority of these attempts has been realized, but by means of scanning the area of interest and not directly viewing the desired area all at once and/or requiring medication to also dilate the pupil of the eye. Pupil dilation creates a level of inconvenience and discomfort for the patient.

More recently, Applicants have developed a digital ophthalmoscope with a contained imaging system that is capable of producing about a 25 degree field of view, using panoramic imaging of the retina. In one version, a smartphone is mechanically supported to the rear of an instrument housing with the imager of the smartphone being positioned in alignment with the contained optical assembly of the instrument or in which the optical assembly is augmented to divert an image to the portable electronic device in order to directly receive captured images.

Still further, it would be advantageous to provide an ophthalmic instrument that provides greater versatility in regard to operation when used in conjunction with a portable electronic device, such as a smartphone or a tablet PC.

BRIEF DESCRIPTION

Therefore and according to a first aspect, there is provided an ophthalmic instrument comprising an imaging assembly having a defined imaging axis and an illumination assembly comprising a source of illumination and having a defined illumination axis, each of the illumination and optical assemblies being disposed within an instrument housing. The instrument including a imaging device wherein the source of illumination creates a focused illumination spot through the pupil that is off axis relative to the optical axis of the instrument and in which the imaging assembly is configured to enable a field of view of at least 40 degrees of the retina of a subject that is directed to the imaging device.

According to at least one version, the imaging system comprises an objective lens and a projection lens, each being disposed along the optical axis and in which the objective lens is sized in order to enable about a 40 degree field of view of the intended target.

According to one version, an imaging device is attachable to the instrument. In at least one embodiment a portable electronic device, such as a smartphone, having a contained electronic imaging element is directly aligned with the imaging assembly along the imaging axis of the instrument when the portable electronic device is attached thereto. According to another embodiment, an electronic imager is disposed within the ophthalmic instrument wherein the images received by the imager can be wirelessly transmitted to a portable electronic device, such as a smartphone or tablet PC, the latter being further configured to control the operation of the ophthalmic instrument. Through this latter form of connection, there is no requirement having to specifically align the imaging element of the portable electronic device with the imaging assembly of the instrument.

According to another version, there is provided a method for enabling increased capability in an ophthalmoscope, the method comprising the steps of:

providing an imaging assembly including an objective lens and a projection lens each disposed commonly along an imaging axis;

providing an illumination assembly having a source of illumination disposed along an illumination axis of the instrument and at least one optical element for causing illumination to be directed through the pupil of a patient's eye and off axis relative to the imaging axis of the instrument and in which a field of view of at least 40 degrees is produced by the imaging assembly and in which an imaging device is configured to receive images from the imaging assembly.

The objective lens is sized to enable the increased field of view wherein the off-axis alignment of the illumination assembly provides sufficient light as a point source to the target while reducing glare-related effects.

According to at least one version a portable electronic device, such as a smartphone, a tablet PC or other device having a contained electronic imager, can be disposed such that the contained imager is aligned along the imaging axis to receive a resulting image. Additional optical elements can be added to adapt to the imaging device, such as to increase magnification and resolution. In another version, an electronic imager can be disposed along the imaging axis to receive an image that can be transmitted wirelessly to a portable electronic device, such as smartphone or a tablet PC, which is either attached to the instrument or located in close proximity thereto.

One advantage provided is that of increased capability in which an ophthalmoscope, configured in the manner described herein, produces a significantly wider field of view to enable similar capabilities of prohibitively more expensive fundus cameras, such as diabetic retinopathy.

Another advantage realized is that enhanced examinations can take place in a doctor's office, enabling proactive diagnoses to be made and in which a field of view of at least 40 degrees can be achieved without medication to dilate the pupil of the eye.

Yet another advantage is that the herein described instrument can be connected and controlled by a portable electronic device that is either directly or indirectly attached to the instrument.

Still another advantage is that the resulting data can be streamed to a "Cloud" service, external peripheral devices, or remote clinical sites using custom software applications.

Yet another advantage is the ability to easily configure the solution to work as a portable instrument, or parked in a chin-rest stand (operated by a practitioner) or a binocular stand (operated by the patient).

These and other features and advantages will be readily apparent from the following Detailed Description, which should be read in conjunction with the accompanying drawings.

BRIEF DESCRIPTION OF THE DRAWINGS

FIG. 5(*b*) is a side elevational view of the illumination and imaging assemblies of the ophthalmoscope of FIG. 5(*a*);

DETAILED DESCRIPTION

This description relates to certain exemplary embodiments of an ophthalmic instrument (i.e., an ophthalmoscope) that is configured to present a suitable (40) degree field of view of a target of interest (i.e., the eye), thereby enabling enhanced examinations to be conducted by a clinician, ophthalmologist, primary physician or other caregiver and as used in conjunction with at least one portable electronic device. It will be apparent that other versions can be created that include the inventive concepts described herein. In addition and throughout the course of this description, various terms are used in order to provide a suitable frame of reference with regard to the accompanying drawings. These terms, such as "distal", "proximal", "upper", "lower", "above", "below", "top", "bottom", "forward" and "backward" however, are not intended to specifically limit or otherwise narrow the scope of the invention, unless where expressly so indicated.

Figure 1:
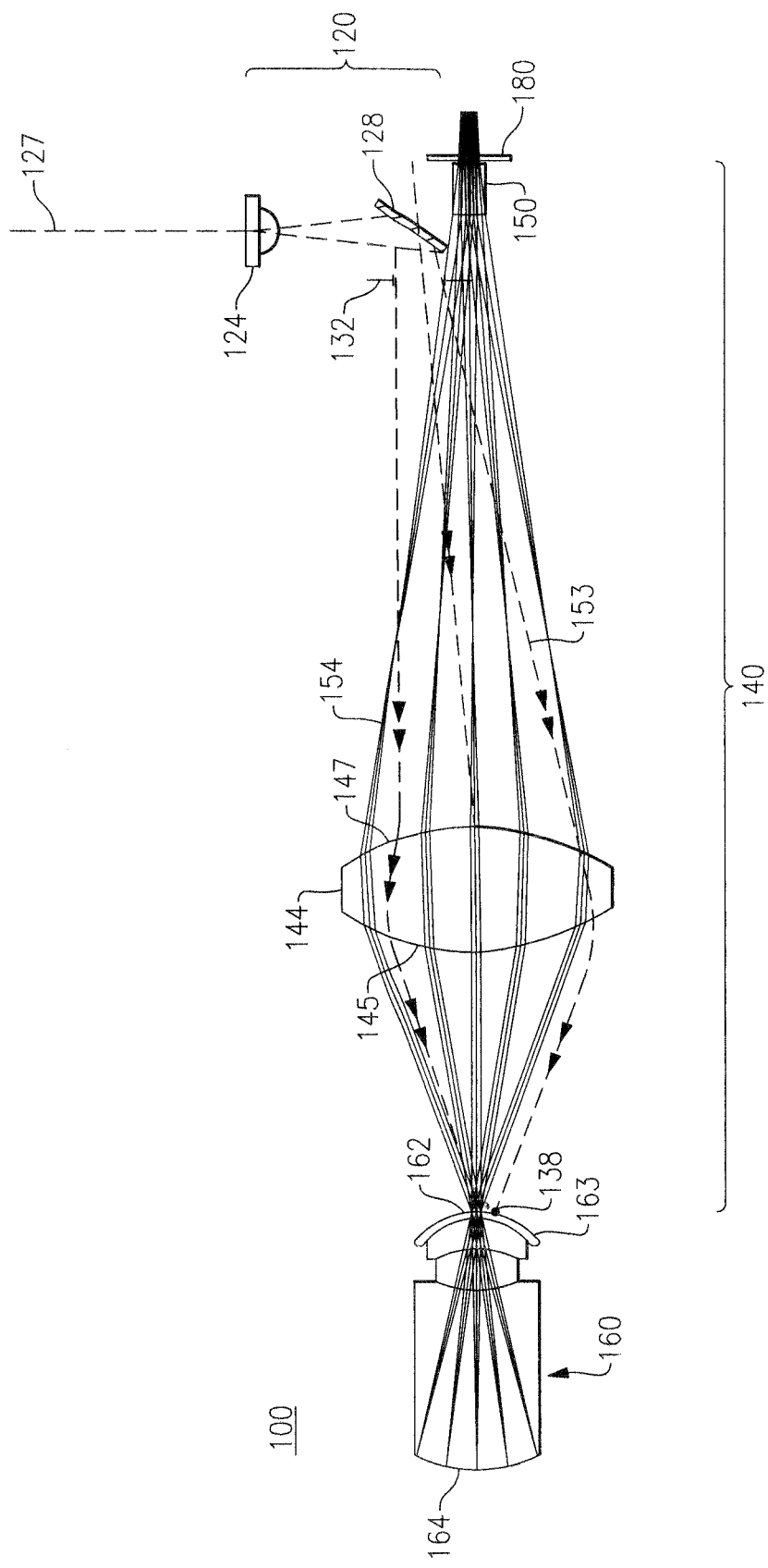
FIG. 1 is a schematic optical layout for an ophthalmoscope configured in accordance with an exemplary embodiment.

Referring to FIG. 1, a schematic system layout of an ophthalmoscope 100 in accordance with a first exemplary embodiment is depicted. The ophthalmoscope 100 (also synonymously referred to throughout as the "instrument") is preferably designed with a housing (not shown in this view) having an interior that is appropriately sized to retain a plurality of components, including an illumination assembly 120 and an imaging assembly 140. According to this embodiment, the illumination assembly 120 includes at least one light source, such as a white or multicolor LED 124, which is fixedly disposed to a circuit board (not shown). According to this embodiment, the LED 124 emits a white light along a defined illumination axis 127. In another version, the LED 124 can emit an amber light, having a wavelength of about 590 nm. The emitted light is caused to impinge upon a reflective surface of a mirror 128 which is angled to direct reflected light toward a distal end of the instrument 100. According to this embodiment, the mirror 128 is angled such that the angle between the viewing axis 158 of the instrument 100 and the illumination axis 127 is approximately 4 degrees. Optionally, a linear polarizer (not shown) can be disposed along the illumination axis 127 between the mirror 128 and the LED 124 in order to reduce the effects of glare.

An aperture stop 132 is disposed distally forward of the mirror 128 along the defined illumination axis 127 and through which light reflected from the mirror 128 is directed toward a target (i.e., the eye, shown herein schematically as 160) of interest, and as discussed herein. According to this embodiment, the aperture stop 132 has a spacing of approximately 1 mm in order to control the amount of reflected light passing therethrough.

Figure 2:
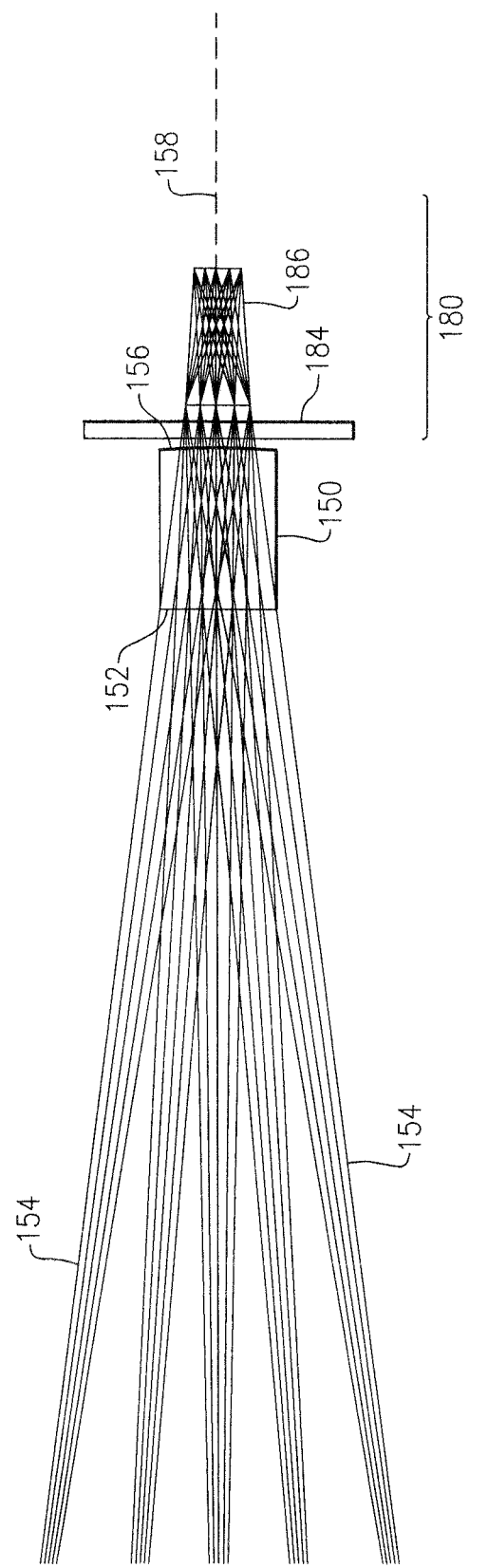
FIG. 2 is an enlarged view of a portion of the imaging assembly of the ophthalmoscope of FIG. 2.

According to this exemplary embodiment, the illumination assembly 120 further includes an objective lens 144 that is centered and aligned along an optical or imaging axis 158, FIG. 2, of the instrument 100. The objective lens 144 is made from an optically clear acrylic according to this version, although other suitable optically materials can be alternatively used, the objective lens 144 being defined by opposing distal and proximal surfaces 145 and 147, respectively. As discussed herein, light 153 passing through the aperture stop 132 is directed for entry through the proximal surface 147 of the objective lens 144 wherein the light is focused and passes through the pupil 162 of the eye (the latter being shown schematically as 160) at an angle relative to the imaging axis 158, FIG. 2, of the instrument 100. A resulting illumination spot, shown schematically as 138, is formed on the cornea 163 and is laterally offset from the imaging axis 158. This light is then further directed and reflected as an image of the back (fundus 164) of the eye 160.

Referring to FIGS. 1 and 2, the imaging assembly 140 of the instrument 100 described herein is defined by the objective lens 144, as well as a projection lens 150, each being disposed along the optical or imaging axis 158 that is coextensive through respective distal and proximal ends of the instrument 100. The objective lens 144 is disposed at an intermediate position along the imaging axis 158 and at a sufficient working distance (WD) from the front of the eye 160. More specifically, the objective lens 144 according to this exemplary embodiment is defined by an outer diameter of approximately 26 mm and a thickness of approximately 12 mm, the distal surface 145 of the objective lens 144 is disposed at a WD of 25 mm from the pupil 162 of the eye 160, and the distance between the proximal surface 147 of the objective lens 144 and a distal surface 152 of the projection lens 150 is about 58-59 mm. The distal surface 145 of the objective lens 144 includes a radius of curvature of 18 mm with a conic constant (K) of −2.3 and the proximal surface 147 has a radius of curvature of −18 mm and a conic constant (K) of −2.3.

Still referring to FIGS. 1 and 2, the projection lens 150 according to this specific embodiment is a section of BK7 crown glass having an outer diameter of approximately 3 mm and an axial length extending along the imaging axis 158 of approximately 4.9 mm. The distal surface 152 of the projection lens 150 is plano and an opposing proximal surface 156 of the projection lens 150 is defined by a radius of curvature of approximately −25.84 mm.

A portable electronic imaging device 180 (shown schematically in FIG. 2), such as smartphone, is disposed at the proximal end of the instrument 100 and proximal to the projection lens 150. The projection lens 150 is disposed forward (distal) of the portable electronic imaging device 180 and aligned therewith along the imaging axis 158.

In terms of operation and according to this exemplary embodiment, illumination light rays, as shown in dashed lines 153, in the form of white light is emitted from the LED 124, reflected from the mirror 128 and directed through the aligned aperture stop 132 toward the distal end of the instrument 100. As noted, the directed light rays 153 passing through the objective lens 144 are focused by this lens 144 and pass through the pupil 162, the latter having a spacing of approximately 2 mm, as an illumination spot 138 that is disposed slightly off axis relative to the imaging axis 158 of the instrument 100. More specifically and according to this embodiment, the formed illumination spot 138 is approximately 1 mm from the imaging axis 158 wherein the illumination spot 138 is focused onto the cornea 163 of a patient's eye 160. Sufficient illumination is provided by the LED 124 to enable reflection of the light from the fundus (retina) of the eye 160.

A set of solid lines 154 depict imaging light rays wherein the reflected light includes an image of the fundus 164 of the eye 150, which is transmitted by outwardly projecting rays from the pupil 162 of the eye 160 as a cone of light through the objective lens 144 along the imaging axis 158 of the instrument 100. Referring to FIGS. 1 and 2, and based on the design of the illumination and imaging assemblies, this cone of light encompasses a 40 degree field of view that is narrowed and passes through the projection lens 150 for transmission to the attached portable electronic imaging device 180, such as a smartphone having a cover glass 184 and an integrated electronic imaging element 186. Each of the LED 124, mirror 128 and aperture stop 132 are disposed out of the imaging path of the herein described instrument 100. More specifically and according to this embodiment, the center of the aligned aperture stop 132 is about 4 mm from the imaging axis 158 of the herein described instrument 100.

As shown in the enhanced view at the proximal end of the imaging assembly 140 according to FIG. 2, the imaging light rays 154 passing through the projection lens 150 are narrowed and caused to pass through the cover glass 184 and are further directed to the retained electronic imaging element 186 of the portable electronic device 180. According to this version, a two lens imaging system is sufficient to create a 40 degree field of view in a compact ophthalmic device. Additionally, at least one linear polarizer (not shown) can be provided along the imaging axis 158 between the projection lens 150 and the imaging device 180 for controlling glare, such as from any of the contained optical elements and eye structures.

Figure 3:
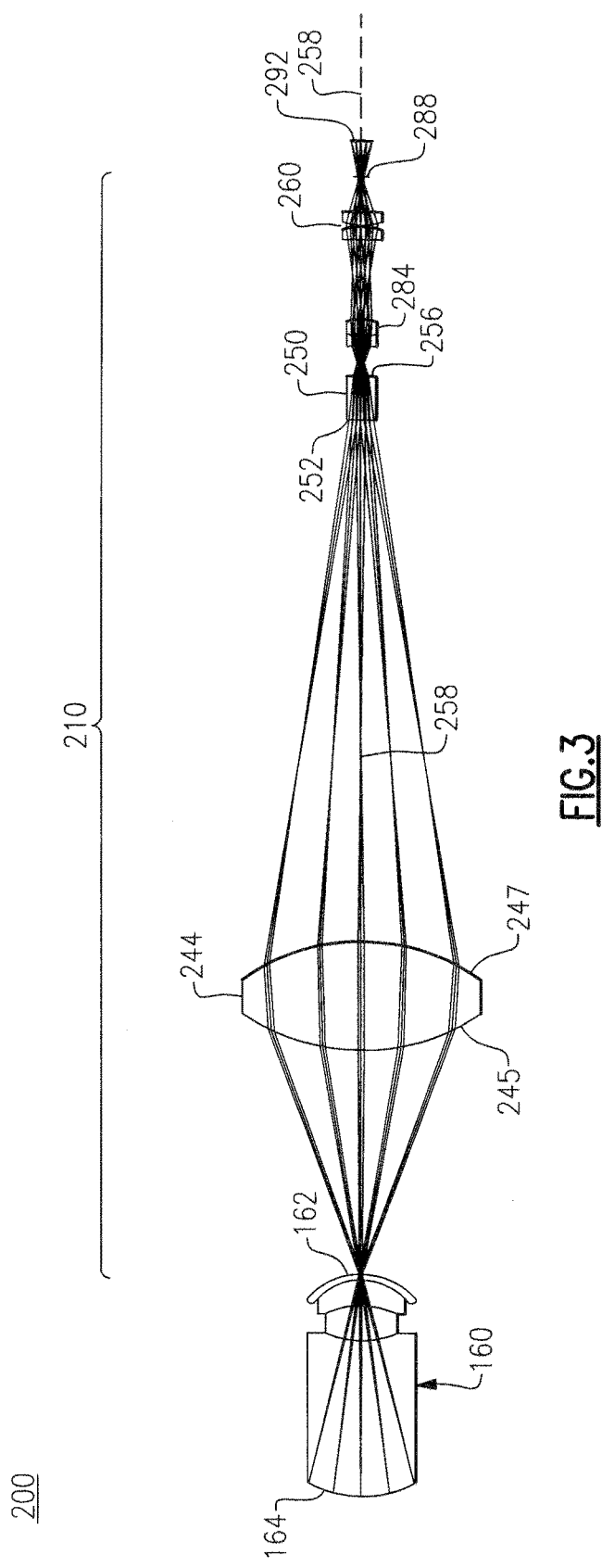
FIG. 3 is a schematic view of an imaging assembly of an ophthalmoscope in accordance with another exemplary embodiment.
Figure 8:
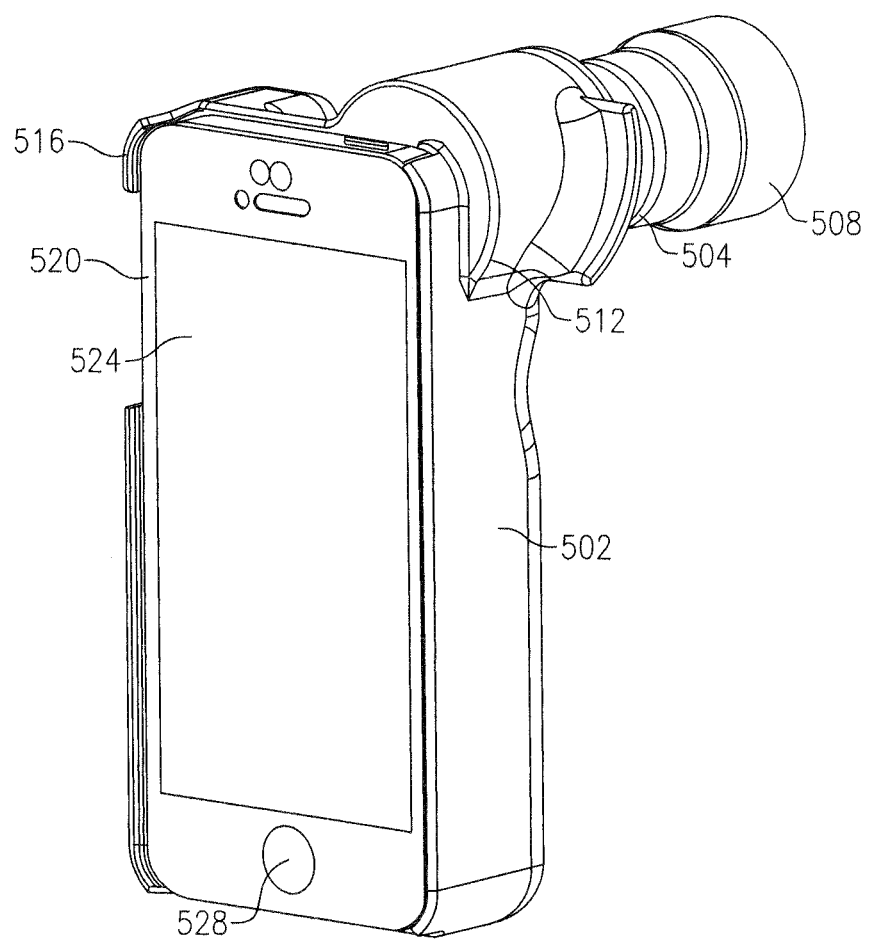
FIG. 8 is a rear perspective view of an ophthalmic instrument housing in accordance with an exemplary embodiment.
Figure 9:
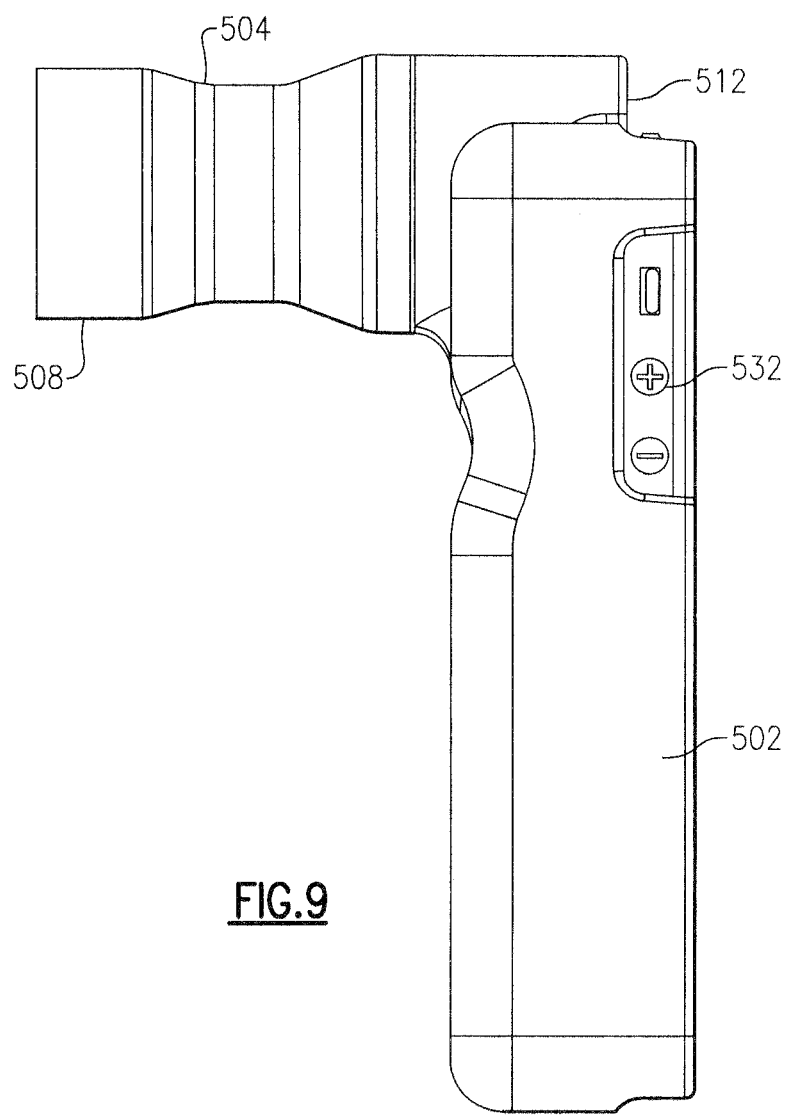
FIG. 9 is a side view, taken in elevation, of the ophthalmic instrument housing of FIG. 8.

While the prior two-lens imaging assembly is highly effective in creating a 40 degree field of view, improvements in resolution and/or magnification can be made. To that end and referring to FIGS. 3 and 4, another exemplary imaging assembly 210 for an ophthalmoscope 200 is herein described. The illumination assembly and the housing of this instrument 200 are each not shown for the sake of clarity. For purposes of this embodiment, however, the illumination assembly can be similar to the version described according to FIGS. 1 and 2 and the instrument housing can be typified, such as depicted in FIGS. 8 and 9 and discussed infra. According to this specific embodiment, the imaging assembly 210 is defined by an objective lens 244 having respective distal and proximal surfaces 245, 247 and a projection lens 250, each commonly disposed and aligned along an imaging axis 258 and in relation to an eye 160, shown schematically only in FIG. 3, of a patient. According to this embodiment, the specific design of each of the foregoing optical elements is identical to the two lens imaging assembly 140, previously discussed with reference to FIGS. 1 and 2 in which reflected light from the eye 160, FIG. 3, is produced as a cone of light that is directed to the objective lens 244, the latter being appropriately sized and positioned to create a suitable (i.e., 40 degrees) field of view, the light being narrowed and further directed to the projection lens 250, in a manner previously described. In addition and according to this exemplary embodiment, a plurality of additional optical elements are provided, each of these elements being disposed in proximal relation to the projection lens 250 along the defined imaging axis 258. These additional optical elements may be assembled integrally as part of the instrument 200 itself or alternatively can be added as a separate module in order to facilitate modification of an existing eye viewing device.

Figure 4:
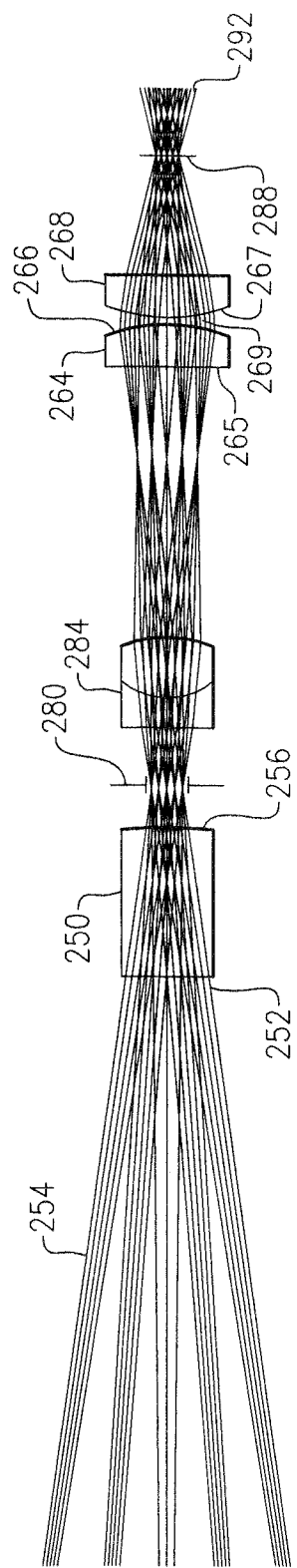
FIG. 4 depicts an enlarged view of a portion of the imaging assembly depicted in FIG. 3.

An enlarged view of the added proximal portion of the exemplary imaging assembly 210 is shown in FIG. 4. More specifically, this assembly 210 comprises the projection lens 250 having a plano distal surface 252 and a curved proximal surface 256, as previously described with regard to the imaging assembly of FIGS. 1 and 2. An aperture stop 280 is disposed between the projection lens 250 and a achromatic doublet 284, such as an Edmund Scientific Model No. 45-089 in which the reflected light rays 254 are further directed along the imaging axis 258 to a pair of imaging lenses 260, including a first lens 264 and a second lens 268. According to this specific embodiment, the imaging lenses 260 are a pair of plano-convex lenses, such as Edmund Scientific Model No. 45-226. The imaging lenses 260 are disposed with a distal plano surface 265 of the first lens 264 facing the achromatic doublet 284 and a distal convex surface 267 of the second lens 268 facing a proximal convex surface 266 of the first lens 264. Each of the first and second lenses 264, 268 are separated by an air gap 269 in which the imaging lenses 260 combine to focus the resulting image to a focal plane 288 and onto an electronic imaging element (not shown) of an attached portable electronic device, shown schematically herein as 292.

Figure 5A:
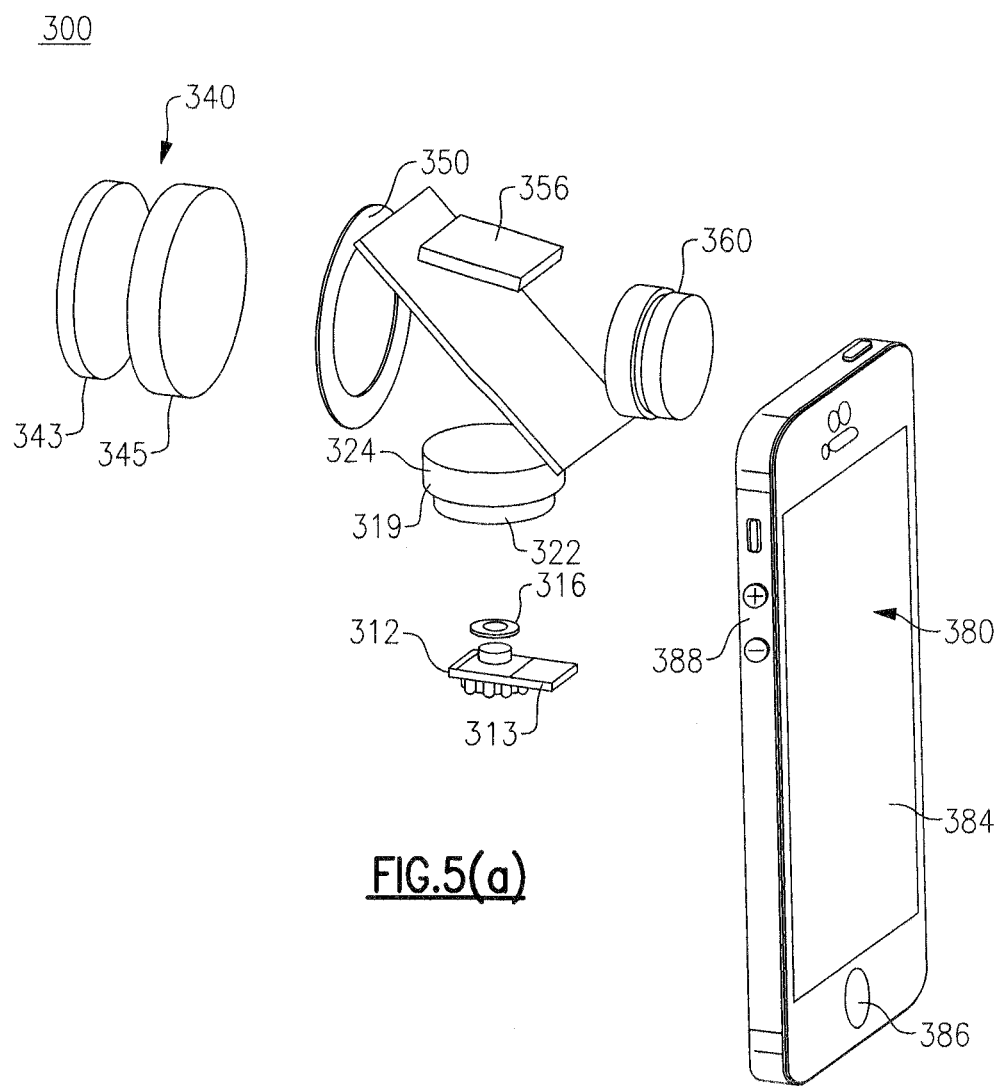
FIG. 5(*a*) is an exploded assembly view of an imaging device, such as a smartphone, and optical components of an ophthalmoscope in accordance with another exemplary embodiment.
Figure 5B:
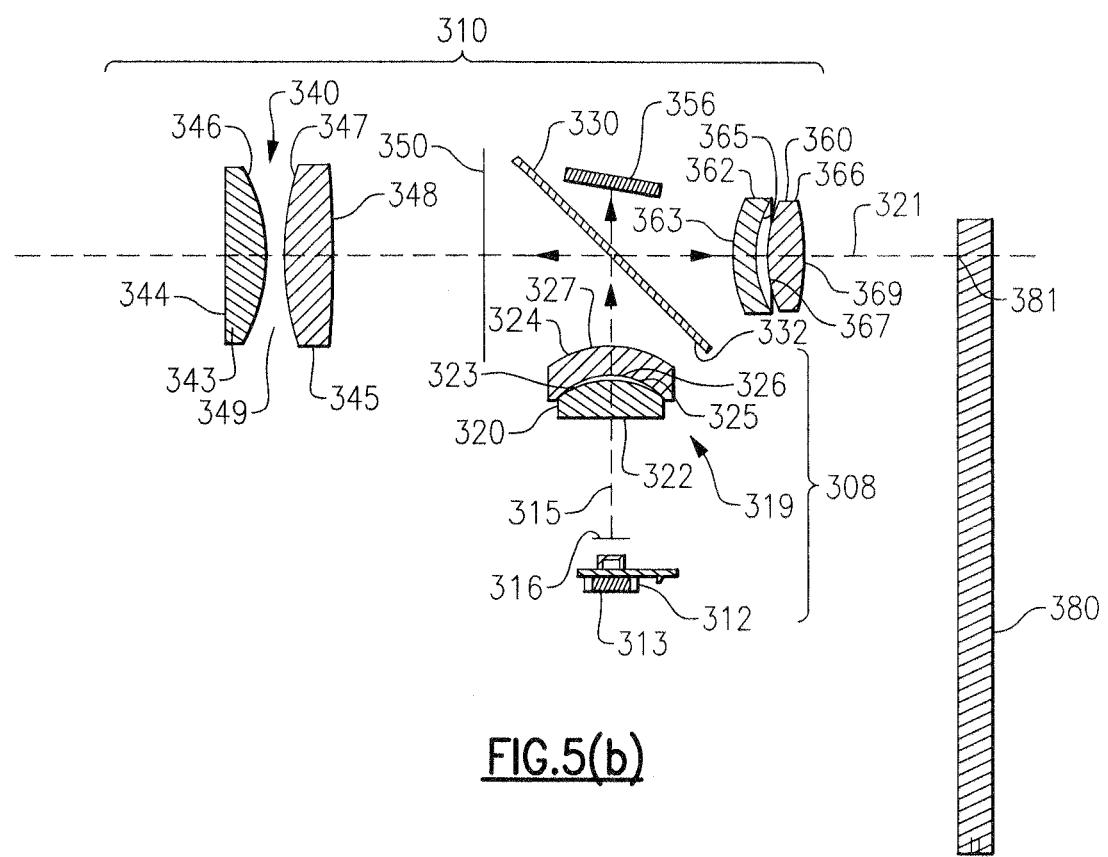
Figure 6:
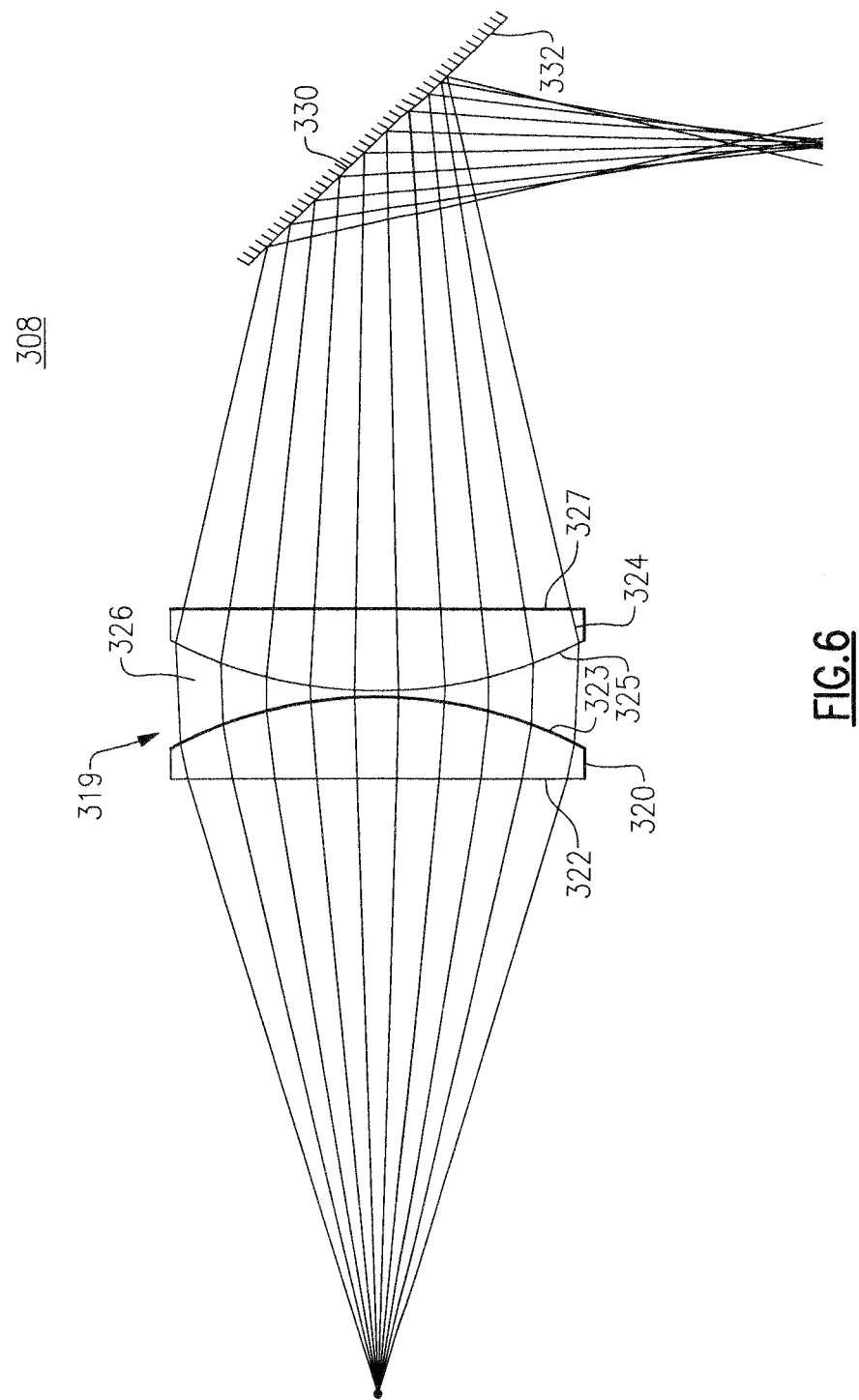
FIG. 6 depicts a schematic layout view of the illumination assembly of the ophthalmoscope of FIGS. 5(*a*) and 5(*b*)

Yet another alternative version of an ophthalmoscope 300 is depicted in FIGS. 5(a), 5(b) and 6. Each of the herein described components can be disposed within a portable housing that enables use with a single hand, such as the housing shown in FIGS. 8 and 9. For purposes of this discussion, however, the instrument housing is not shown in order to better describe the salient features/components of the various illumination and imaging assemblies.

As in the preceding exemplary embodiments that have been described, this ophthalmoscope 300 includes an illumination assembly 308 and an imaging assembly 310, each being disposed within the instrument housing (not shown). The illumination assembly 308 comprises a white or multi-color LED 312 that is configured to be mounted, for example, to a printed circuit board 313. As previously noted, the LED 312 can preferably emit an amber light capable of emitting a light having a wavelength of approximately 590 nm. An aperture stop 316 is disposed a predetermined distance in front of the LED 312 and aligned along a defined illumination axis 315, as shown in FIGS. 5(b) and 6. The aperture stop 316, according to this exemplary embodiment, is disposed 3.5 mm in front of the LED 312 and defined by a spacing of approximately 2.8 mm. A set of condensing lenses 319 is further aligned with the LED 312 along the illumination axis 315 and disposed in front (forward) of the aperture stop 316. According to this specific embodiment, the set of condensing lenses 319 comprise a first lens 320 and an axially adjacent lens 324 that are aligned along the illumination axis 315 between the aperture stop 316 and a beamsplitter 330, the latter optical element also being disposed along a defined optical or imaging axis 321 of the herein described instrument 300. According to this specific embodiment and with reference to FIG. 6, the first lens 320 is defined by a plano proximal or back surface 322 facing the LED 312 and a opposing distal surface 323, the latter having a radius of curvature of approximately 14.5 mm. The second adjacent lens 324 has a proximal surface 325 facing the first lens 320 that has a radius of curvature of approximately 19.4 mm and a opposing distal surface 327 facing the beamsplitter 330 having a radius of curvature of approximately 22.5 mm. The lenses 320 and 324 are separated by an air gap 326, which according to this specific embodiment is approximately 1.4 mm. The beamsplitter 330 includes an angled surface 332 disposed in relation to the illumination axis 315 and configured to reflect light emitted from the LED 312 in order to direct the emitted light toward the distal end of the instrument 300. According to this embodiment, the center of the angled surface 332 is spaced approximately 18 mm from the distal surface 327 of the second lens 324.

Though not shown, light that is reflected from the angled surface 332 of the beamsplitter 330 is directed through a set of objective lenses 340 that combine to focus the light through the pupil of a patient's eye (not shown) and at an angle relative to the imaging axis 321 of the instrument 300. As in the preceding, the light reflected from the angled surface 332 is first directed through an aperture stop 350. The light passing through the objective lens 340 is narrowed and focused as an illumination spot on the cornea of the eye that is slightly offset laterally relative to the imaging axis 321 of the instrument 300. The remaining illumination directed through the beamsplitter 330 impinges upon a light sink or trap 356 in order to prevent back reflection or glare produced by the light source 312, condensing lenses 319 or beamsplitter 330. The light sink 356 is formed from a light absorbing material such as strongly absorbing glass, black paint or other suitable material.

Referring to FIGS. 5(a) and 5(b), the imaging assembly 310 of this exemplary instrument 300 comprises a series of optical elements that are aligned and configured along the defined imaging axis 321 to guide a resulting reflected image from the back of the eye (not shown) to an attached imaging device (e.g., a smartphone 380 having a liquid crystal display 384, and actuable buttons 386, 388). These optical elements include the set of objective lenses 340 as well as a set of imaging lenses 360, the latter optical elements being disposed proximally in relation to the beamsplitter 330. According to this specific embodiment, the set of objective lenses 340 is defined by a first lens 343 and a second lens 345, each of these lenses 343, 345 being separated by an air gap 349. More specifically and according to this embodiment, the first lens 343 is defined by an outer diameter of 34 mm and an axial length of approximately 8 mm and the second lens 345 is defined by an outer diameter of 36.5 mm and an axial length of approximately 9.5 mm. The first lens 343 includes a distal surface 344 having a radius of curvature of approximately 340 mm and a proximal surface 346 having a radius of curvature of approximately 36.8 mm. The second adjacent lens 345 of the set 340 is defined by a distal surface 347 having a radius of curvature of approximately 59.6 mm and a proximal surface 348 having a radius of curvature of approximately 253 mm. The air gap 349 separating the first and second lenses 343, 345 is approximately 3.9 mm. According to this exemplary embodiment, the working distance (WD) between the front of the eye (not shown) of the patient and the distal surface 344 of the first lens 343 is approximately 38 mm.

The aperture stop 350 is disposed between the objective lens 350 and the beamsplitter 330. According to this embodiment, the aperture stop 350 has an opening of approximately 27.8 mm to prevent the passage of stray light.

The imaging lenses 360 according to this specific embodiment are also defined by a pair of spaced lenses 362, 366, each of the lenses being aligned along the defined imaging axis 321 and in proximal relation to the beamsplitter 330. The first imaging lens 362 according to this embodiment is defined by a distal surface 363 having a radius of curvature of approximately 26.9 mm and a proximal surface 365 having a radius of curvature of approximately 19.1 mm. The second lens 366 is defined by a distal surface 367 having a radius of curvature of approximately 27.4 mm and a proximal surface 369 having a radius of curvature of approximately 55.2 mm. The outer diameter of the second lens 366 is approximately 20.8 mm wherein the first lens 362 has an axial length of approximately 4.5 mm and the second lens 366 has an axial length of approximately 7.0 mm in which an air gap 370 provided between the first and second lens 362, 366 provides a separation of approximately 2.4 mm.

The herein described imaging assembly 310 can be axially aligned with the contained camera 381 (shown schematically in FIG. 5(b) of the smartphone 380 and supported within the instrument 300 by suitable means, such as, for example, a support member (not shown) having a peripheral grooved area that is sized to receive the side surfaces of the smartphone 380. According to this embodiment, the overall distance between the proximal (rear) wall of the imaging device 380 and the distal most optical element of the set of objective lenses 340 is approximately 152 mm. The distance between the cover glass (not shown) of the imaging device 380 and the proximal surface 369 of the second imaging lens 366 is approximately 30 mm.

As in the preceding, the herein described illumination and imaging assemblies are configured in order to create at least a 40 degree field of view that can be suitably imaged and enable enhanced examinations, such as diabetic retinopathy, to be performed by a caregiver and viewed for example on the display 384 of the attached smartphone 380.

Figure 7:
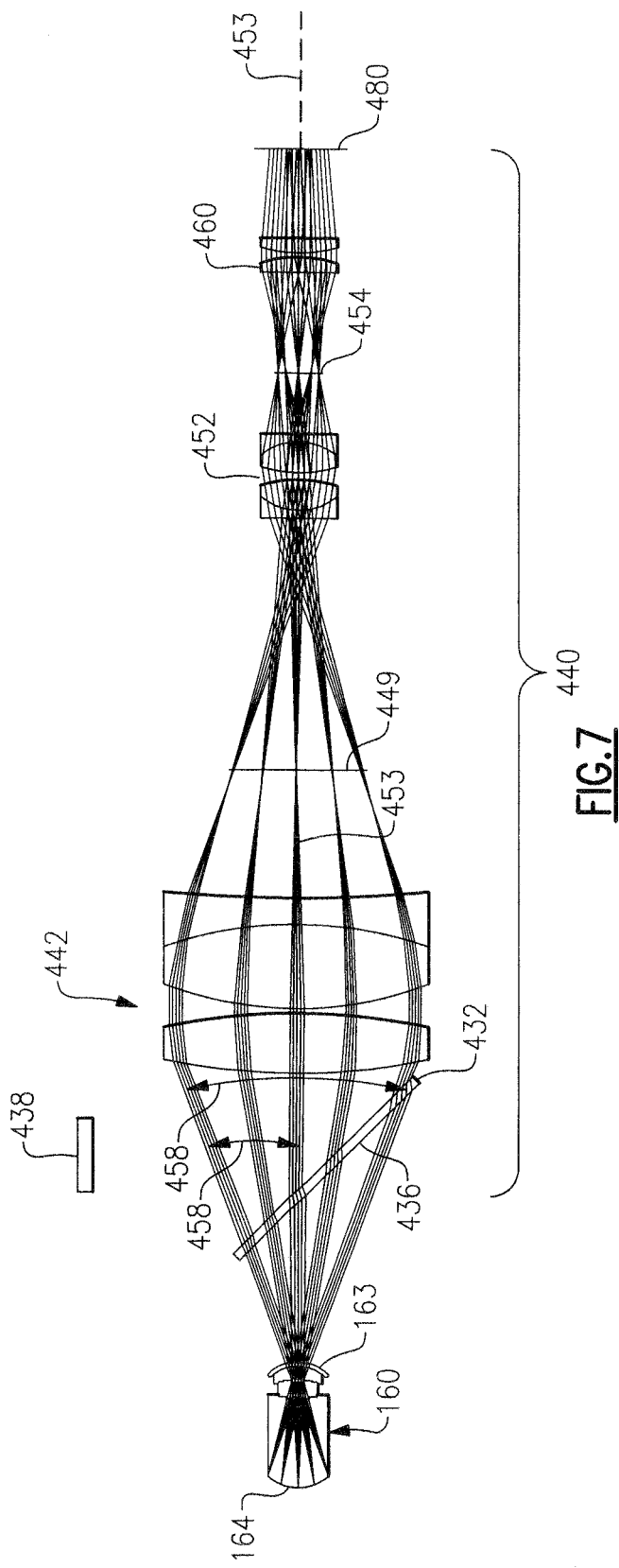
FIG. 7 is a schematic optical layout of an ophthalmoscope in accordance with an alternative embodiment.

Yet another alternative exemplary embodiment is herein described schematically with reference to FIG. 7. According to this version, an ophthalmoscope 400 includes a housing (not shown for clarity but typified by those depicted, for example, in FIGS. 8 and 9) that retains an illumination assembly (also not shown in this view), as well as an imaging assembly 440.

As in the preceding embodiment, the illumination assembly of this instrument 400 can include an LED that emits white, amber or other colored light, an aperture stop and a set of condensing optics, each being aligned along a defined illumination axis. According to this exemplary embodiment, a beamsplitter 432 is axially aligned with each of the foregoing elements, the beamsplitter 432 having an angled surface 436 that is configured to direct light to the pupil 162 of a patient's eye 160 as an illumination spot (not shown). A light sink or trap 438 aligned with the beamsplitter 432 is configured to receive excess illumination that is transmitted through the beamsplitter 432. The light sink 438 is formed from a light absorbing material such as strongly absorbing glass, black paint or other suitable material and is configured to reduce the incidence of glare or back reflection in the instrument 400 from the light source 424 or beamsplitter 432.

The imaging assembly 440 according to this exemplary embodiment includes an objective lens doublet 442 that is disposed proximally (i.e., behind) the beamsplitter 432 and aligned along the defined imaging axis 453. The objective lens 442 is sized and configured to create a suitable field of view (40 degrees).

According to this embodiment, the imaging assembly 440 further includes a set of relay lenses 452 as well as a set of imaging lenses 460, respectively, each of the latter being linearly disposed along the imaging axis 453 proximal to the objective lens 440 and distally arranged in relation to an electronic imaging device 480, such as a CCD or a CMOS that can be attached to the proximal end of the instrument 400. The electronic imaging device 480 can be provided as part of a separate device, or can be integral to the instrument 400 itself, being preferably disposed in a proximal end of the instrument head (not shown) and aligned with the relay lens 452, imaging lens 460 and other optical components of the imaging assembly 440 along the defined imaging axis 453.

According to this embodiment, the beam splitter 432 is disposed distally forward of the objective lens 442 and along the imaging axis 453 of the instrument 400. The beam splitter 432 is aligned with the light source 424 and is angled approximately 40 degrees relative to the imaging axis 453, as depicted by arrows 458.

In use and referring to FIG. 7, the light source (not shown) emits light that passes through the condensing lenses (not shown) and impinges onto the angled surface 436 of the beam splitter 432 along a defined illumination axis. A portion of the emitted illumination is reflected from the angled surface 436 of the beam splitter 432 and toward the eye 160 of the patient, the latter being shown in schematic form, wherein an illumination spot (not shown) is caused to be directed through the pupil at an angle relative to the imaging axis 453 and focused upon front of the eye 160. The portion of the emitted illumination passes through the beam splitter 432 and impinges upon the light sink 438, which traps any residual illumination and prevents glare or back reflection within the herein described instrument 400.

As opposed to the previously described instrument and according to this version, a reflected image of the retina 164 is sequentially directed through the pupil 162 along the imaging axis 453 of the instrument 400, through the beamsplitter 432 and subsequently through the objective lens 442. This latter optical element 442 is appropriately sized to create a field of view of 40 degrees wherein the transmitted image is transmitted through a first retinal focal plane 449 and subsequently through the relay lens 452 and a second conjugate retinal focal plane 454 in which the relayed image is transmitted through the imaging lens 460 to the proximal end of the instrument 400 and according to this exemplary embodiment to an electronic imaging element 480, such as either directly made integral to the instrument 400 or as part of a smartphone or other portable imaging device.

Referring to FIGS. 8 and 9, an exemplary instrument 500 is depicted having an instrument body 502 and an instrument head 504. The instrument head 502 and body 504 are defined by an interior that is appropriately sized to retain the illumination and imaging assemblies discussed herein, as well as an electronic imaging device, such as a smartphone 520 that can be releasably attached within a receptacle 516 provided at the proximal end 512 of the instrument body 502. When attached, the retained camera of the attached imaging device 520 is aligned with the imaging axis of the instrument 500, the latter axis extending through the major dimension of the instrument head 504 extending between a distal end 508 and proximal end 512. According to this embodiment and when attached, the rear of the device 520 is completely accessible, including the display 524 and the control button 528. In addition and according to this embodiment, a lateral portion of the receptacle 516 is removed to permit access to other control features of the attached device 520 wherein captured images of the eye can be displayed.

Figure 10:
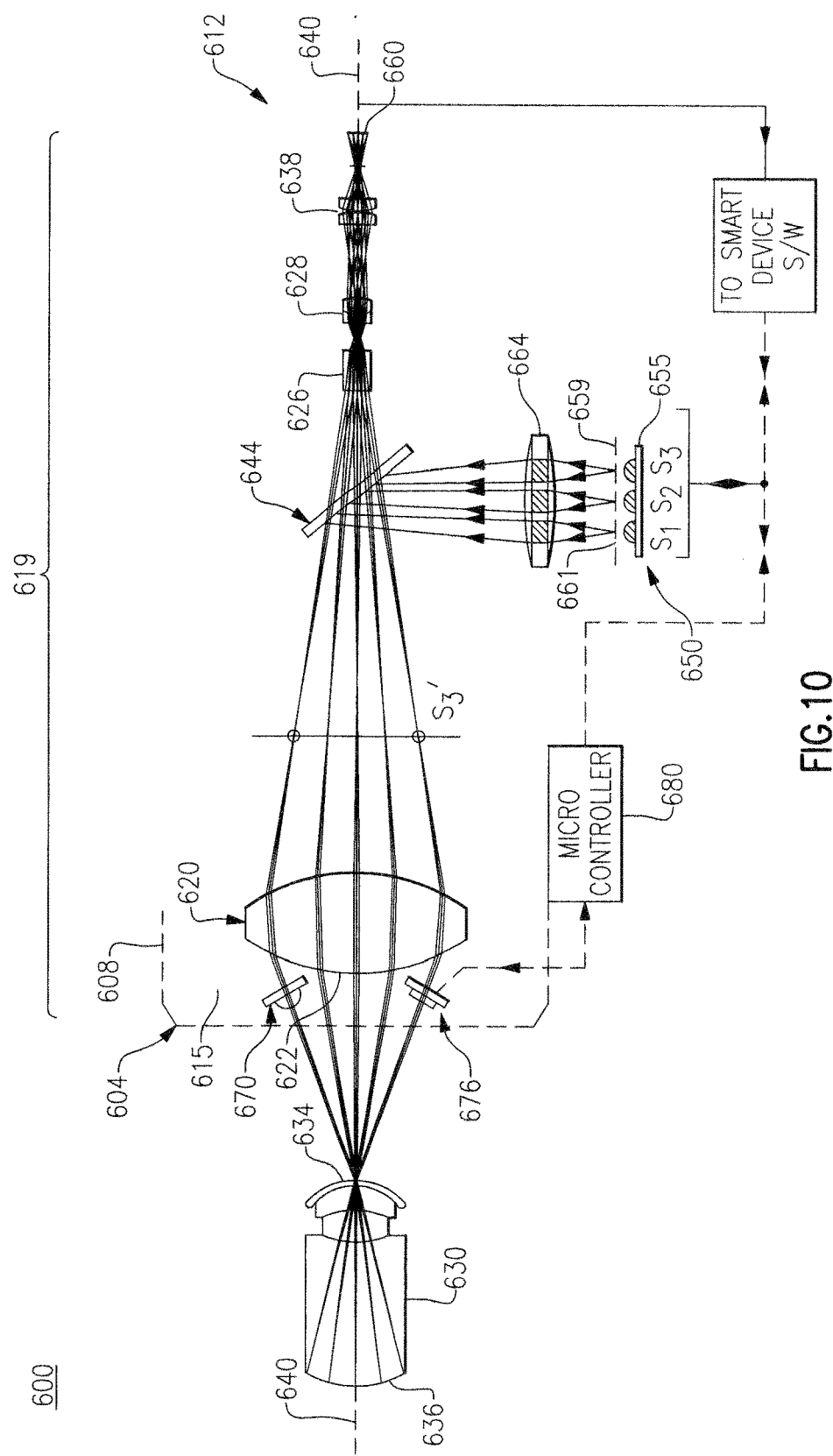
FIG. 10 is a schematic optical layout of an ophthalmic instrument made in accordance with another exemplary embodiment.

Yet another exemplary embodiment of an ophthalmic instrument 600 is provided with reference to FIG. 10. The ophthalmic instrument 600 is defined by an instrument housing 604, a front end 608 being shown in phantom and an opposing rear or proximal end 612, the instrument housing 604 being further defined by an interior 615 that is appropriately sized for retaining a plurality of components. According to this version, an optical imaging assembly 619 comprises an objective lens 620 that is positioned adjacent the front end 608 of the instrument housing 604 and a projection lens 626 positioned proximally therefrom along the imaging axis 640 of the instrument 600. The two lenses 620 and 626 are sized and configured to create a suitable field of view (40 degrees) of a target, which according to this embodiment is an eye 630, shown schematically and including a pupil 634 and a retina 636 in the manner previously described.

According to this embodiment, the imaging assembly 619 further includes a set of relay lenses 628 as well as a set of imaging lens 638, respectively, each of the latter components being linearly disposed along the defined imaging axis 640 and in proximal relation to the projection lens 626 and distally in relation to an electronic imaging device 660, such as a CCD or a CMOS that can be attached to the proximal end 612 of the instrument housing 604. For purposes of this embodiment, the electronic imaging device 660 can be provided as part of a separate device, or can be integral to the instrument 600 itself, the imaging device 660 being aligned with the relay lens 628 and imaging lens 638 along the defined imaging axis 640.

A window 644 manufactured from an optically transmissive material or a beamsplitter is further aligned along the imaging axis 640 of the instrument 600 between the objective lens 620 and the projection lens 626 with the window 644 being acutely angled in relation to an illumination array 650 that is disposed along an illumination axis 654 of the instrument 600. A plurality of LEDs, herein labeled as S1, S2 and S3 are defined in the illumination array 650, although the specific number of LEDs utilized can be easily varied. The LEDs according to this embodiment are disposed in a side by side fixedly mounted relation on a circuit board 655 or similar substrate, each LED being configured to emit an amber light having a wavelength of approximately 590 nm. An aperture mask 659 having a series of appropriate sized holes 661 is disposed onto the illumination array 650, the holes 661 being aligned with the corresponding LEDs S1, S2, S3 of the array 650, specifically guiding light to a projection lens 664, which is distally disposed along the defined illumination axis 654. As shown, light from the illumination array 650 is directed through the holes 661 in the aperture mask 659 and through the projection lens 664, the emitted light being reflected by the window 644 towards the objective lens 620. According to this embodiment, an infrared LED 670 is disposed adjacent the distal side 622 of the objective lens 620 in relation to an outer diametral portion thereof. An infrared photodiode 676 is also provided in relation to an outer diametral portion of the objective lens 620, the photodiode 676 being disposed on an opposite side of the imaging axis 640 relative to the infrared LED 670. Each of the infrared LED 670 and the photodiode 676 are inwardly angled toward the front panel of the instrument housing 604 at its distal end 608. According to this embodiment and as schematically shown, the photodiode 676 is electrically connected to a microcontroller 680, the latter being connected to the LED array 650 and the portable electronic device 660.

In operation, the infrared LED 670 and the photodiode 676 are positioned such that light from the infrared LED 670 can be directed to the eye 630 and more specifically the pupil 634 of the patient, with light being reflected from the pupil 634 to the photodiode 676 only if the instrument 600 is set at a predetermined working distance (Z), which according to this embodiment is approximately 25 mm. The infrared LED 670 and the photodiode 676 herein provide an LED fixation path prior to initiating light from the illumination array 650. According to this exemplary embodiment and if the instrument 600 is set at the correct working distance to the eye 630 (to the pupil 634 of the eye), a signal from the photodiode 676 indicative of the receipt of reflected light from the eye 630 is provided to the microcontroller 680 and the illumination array 650 is enabled for use. If the photodiode 676 fails to receive an adequate amount of reflected light indicative that the instrument 600 is either in excess or inside of the proper working distance, the LEDs S1, S2, S3 of the illumination array 650 are caused to blink or to produce another effect that can be visually perceived by the user of the instrument 600. Alternatively, the illumination array can be rendered inoperative until the proper working distance has first been established.

Once the proper working distance (Z) has been established, the illumination array 650 produces an amber or other appropriately colored light that is transmitted to the eye 630, as reflected by the window 644 and transmitted through the objective lens 620. Reflected light from the retina 636 at the back of the eye 630 is transmitted through the objective lens 620, having provided a 40 degree field of view in which the light is transmitted through a retinal image plane through the window 644, the projection lens 626 and the remainder of the imaging assembly 619 to the portable electronic device 660 in the manner previously discussed.

Figure 11:
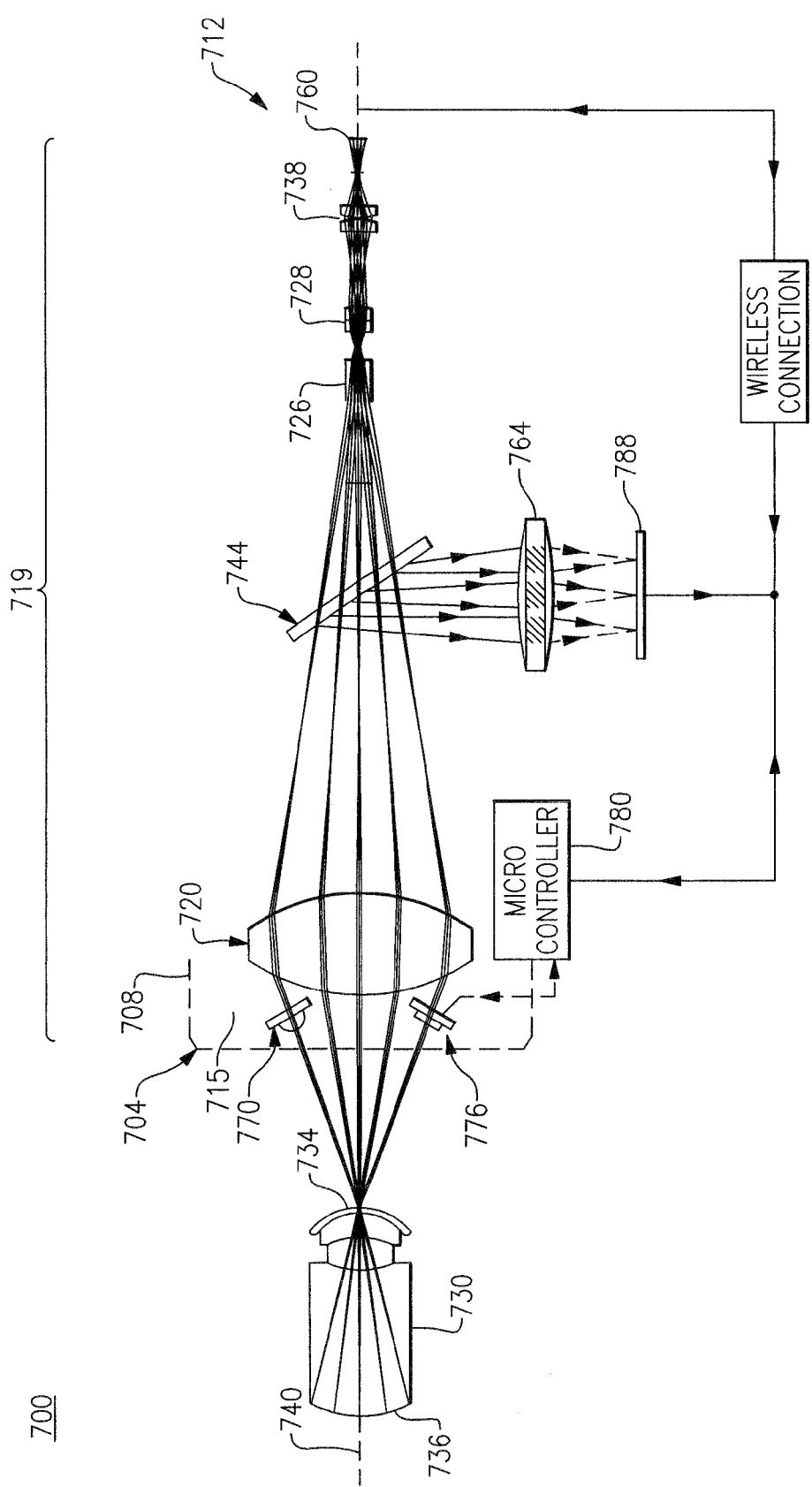
FIG. 11 is a schematic optical layout of an ophthalmic instrument made in accordance with yet another exemplary embodiment.

According to yet another exemplary embodiment and with reference to FIG. 11, there is shown another version of an ophthalmic instrument 700. As in the prior version, the instrument 700 is defined by an instrument housing 704, shown in phantom and only in part, the housing 704 having a front or distal end 708 and a rear or proximal end 712 and in which the housing 704 is further defined by an appropriately sized interior 715. An imaging assembly 719 arranged in fixed relation within the interior 715 of the instrument housing 704 comprises an objective lens 720 that is disposed adjacent the distal end 708 of the instrument housing 704 and a projection lens 726 proximally disposed along an imaging axis 740. Each of the foregoing optical components are similar in terms of design and function to those described in prior embodiments. The imaging assembly 719 further includes a set of relay lenses 728 as well as a set of imaging lenses 738, each of the foregoing being aligned along a defined optical or imaging axis 740, respectively. These latter optical elements according to this exemplary embodiment are defined similarly to those described in FIGS. 7 and 10 in terms of their overall function and design and are similarly aligned in proximal relation to the projection lens 726 and distally aligned along the imaging axis 740 relative to the imager of a first portable electronic device or "smart device" 760, which can for example be an iphone or similar device. In this specific embodiment, a separate second electronic imaging device 788 is aligned off axis relative to the imaging axis 740 wherein a beamsplitter 744 is disposed to direct an image obtained through a condensing lens 764 and direct same to the imaging device 788. This separate electronic imaging device 788 enables a user, such as physician or clinician, to obtain an advance or preview mode of the intended target (e.g., eye 730) prior to actual operation. As in the prior described embodiment, the operation of the ophthalmic instrument 700 according to this exemplary embodiment is also predicated upon establishing a suitable working distance (Z) as measured between the instrument 700 and the eye 730 of the patient. An infrared LED 770 is disposed in relation to an infrared photodiode 776, wherein the LED 770 and photodiode 776 are disposed on opposing sides of the imaging axis 740 of the herein described instrument 700 at an outer diametral portion of the objective lens 720 with the output of the photodiode 776 being linked to a microcontroller 780.

According to this version, the wireless imager 788 can be a Sony QX10 or Sony QX100 camera or other wirelessly connected imaging device that is linked with the display of the smart device 760. The reception of a signal from the photodiode 776 is linked to the microcontroller 780, whose output can be shown on the display of the smart device 760, indicating an "out of range" or "in range" signal to the user. Given the application of the preview mode described herein, this specific instrument 700 is preferably a bench top apparatus as opposed to being used for hand-held operation.

Figure 12:
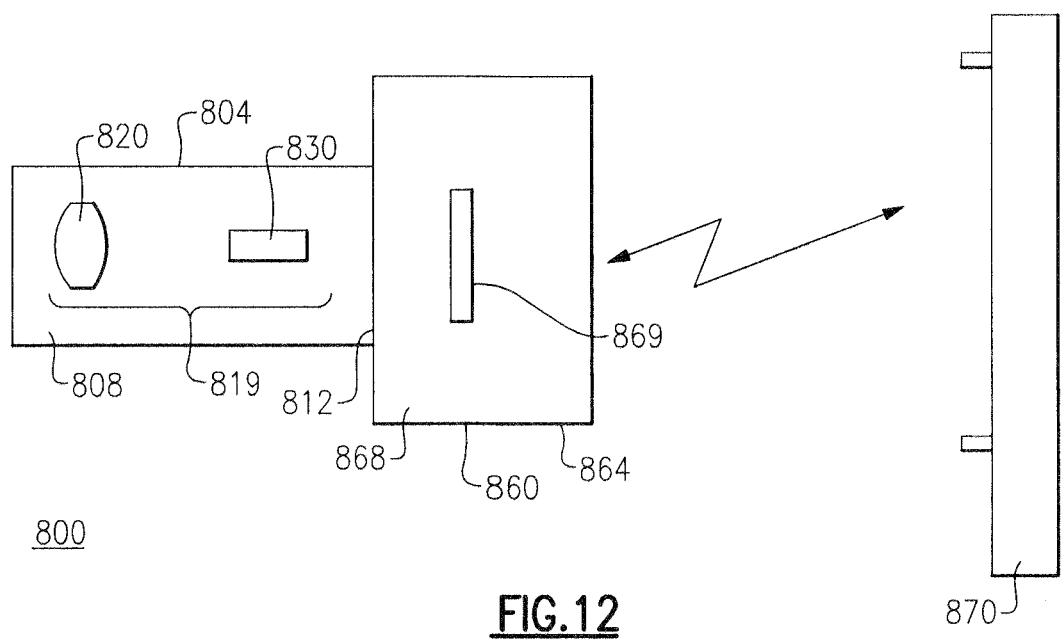
FIG. 12 is a schematic block diagram of an ophthalmic instrument made in accordance with yet another exemplary embodiment.

It should be noted that each of the foregoing instrument or instrument system designs can commonly include a portable electronic device (e.g., a tablet PC, smartphone) that is integrated directly as part the imaging assembly of the herein described instrument or otherwise as an attached device, as shown for example in FIGS. 8 and 9 in which alignment is required between the respective optical systems/assemblies of both the portable electronic device and the instrument based upon some form of mechanically interconnection that specifically achieves the desired alignment. Referring to FIG. 12, there is schematically depicted an ophthalmic diagnostic instrument made in accordance with yet another exemplary embodiment.

The ophthalmic instrument 800 according to this exemplary embodiment is defined by a housing 804 having an interior that is appropriately sized for retaining a plurality of components, including an imaging assembly 819 that enables a 40 degree (or greater) field of view of the eye (not shown) of a patient, as previously discussed, the imaging assembly 819 including an objective lens 820 disposed at a distal end 808 of the instrument housing 804 and a projection lens 830, each aligned along a common imaging axis 840. A mobile electronic camera 860, such as a Sony QX10 or a Sony QX100 mobile camera, is further configured and aligned with the imaging assembly 819 along the defined imaging axis 840. The mobile electronic camera 860 is defined by an enclosure 864 having an interior 868 that is sized to retain an electronic imager 869 as well as a mechanism that enables dynamic optical focusing, the imager 869 being aligned to receive the images from the imaging assembly 819 and then wireless transmit the captured images to a portable electronic device 870, such as a smartphone or tablet PC, which is remotely located using a convenient communication protocol, such as Bluetooth. The enclosure 869 is further configured for releasable attachment to the front or distal side of the portable electronic device but since the images are wirelessly transmitted there is no requirement for optical alignment when the device is attached to the portable electronic device 870.

In this latter embodiment, the operation of the ophthalmic instrument 800, including the electronic mobile camera 860, can be controlled using software that is resident in the portable electronic device 870 such as through the user interface of the portable electronic device 870. Advantageously and according to this exemplary embodiment, the electronic imager contained within the portable electronic device 870 does not have to be aligned with the instrument 800, thereby providing additional versatility in which the portable electronic device 870 can be located remotely from the patient.

PARTS LIST FOR FIGS. 1-12

- 100 ophthalmoscope (instrument)
- 120 illumination assembly
- 124 LED
- 127 illumination axis
- 128 mirror
- 132 aperture stop
- 138 illumination spot
- 140 imaging assembly
- 144 objective lens
- 145 distal surface, objective lens
- 147 proximal surface, objective lens
- 150 projection lens
- 152 distal surface, projection lens
- 153 illumination light rays
- 154 imaging light rays
- 156 proximal surface, projection lens
- 158 imaging axis
- 160 eye
- 162 pupil
- 163 cornea
- 164 retina
- 180 electronic imaging device
- 184 cover glass
- 186 electronic imaging element
- 200 ophthalmoscope (instrument)
- 210 imaging assembly
- 244 objective lens
- 245 distal surface, objective lens
- 247 proximal surface, objective lens
- 250 projection lens
- 252 distal surface, projection lens
- 254 light
- 256 proximal surface, projection lens
- 258 imaging axis
- 260 imaging lenses
- 264 first imaging lens
- 265 distal surface, first imaging lens
- 266 proximal surface, first imaging lens
- 267 distal surface, second imaging lens
- 268 second imaging lens
- 269 air gap
- 280 aperture stop
- 284 doublet, achromatic
- 288 focal plane
- 292 electronic imaging element
- 300 ophthalmoscope (instrument)
- 308 illumination assembly
- 310 imaging assembly
- 312 LED
- 313 circuit board
- 315 illumination axis
- 316 aperture stop
- 319 condensing lenses
- 320 first lens
- 321 imaging axis
- 322 proximal surface, first lens
- 323 distal surface, first lens 324 second lens
325 proximal surface, second lens
326 air gap
327 distal surface, second lens
330 beamsplitter
332 angled surface
340 set of objective lenses
343 first lens
344 distal surface, first lens
345 second lens
346 proximal surface, first lens
347 distal surface, second lens
348 proximal surface, second lens
349 air gap
350 aperture stop
356 light trap or sink
360 imaging lenses
362 first lens
363 distal surface, first lens
365 proximal surface, first lens
366 second lens
367 distal surface, first lens
369 proximal surface, second lens
380 portable electronic device (smart device)
381 camera imager
384 LCD display, smart device
386 actuable button, smart device
388 actuable buttons
400 ophthalmoscope
432 beamsplitter
436 angled surface
438 light trap
440 imaging assembly
442 objective lens
449 focal plane
450 aperture stop
452 relay lens
453 imaging axis
454 retinal focal plane
458 arrows
460 imaging lens
480 imaging device
500 instrument
502 instrument housing
504 instrument head
508 distal end
512 proximal end
516 receptacle
520 smart phone
524 display
528 control buttons
532 control buttons
600 instrument
604 housing, instrument
608 front or distal end
612 rear or proximal end
615 interior
619 imaging assembly
620 objective lens
622 distal side, objective lens
626 projection lens
628 relay lens
630 eye
634 cornea
636 retina
638 imaging lens
640 imaging axis
644 window or beamsplitter
650 LED array
655 circuit board or substrate
659 aperture mask
660 electronic imaging device
661 holes
664 projection lens, fixation target
670 LED, infrared
676 photodiode, infrared
680 microcontroller
700 ophthalmic instrument
704 housing (partially in phantom)
708 front or distal end
712 rear or proximal end
715 interior
719 imaging assembly
720 objective lens
726 projection lens
728 relay lens
730 eye
734 cornea
736 retina
738 imaging lens
740 imaging axis
760 first portable electronic device/smart device
764 condenser lens
770 infrared LED
776 photodiode
780 microcontroller
788 second or preview imaging device
800 instrument
804 housing
808 distal end
812 proximal end
819 imaging assembly
820 objective lens
830 projection lens
860 mobile camera
864 enclosure
868 interior
869 imager
870 portable electronic device
S1 LED
S2 LED
S3 LED
Z working distance It will be readily apparent to those of sufficient skill that other modifications and variations are possible based on the inventive ambits described herein, as well as the appended claims.

The invention claimed is:
1. An ophthalmoscope comprising:
  a housing having a proximal end, a distal end and an interior;
  an imaging assembly including a plurality of optical elements disposed along an imaging axis, the imaging assembly including an objective lens proximate the distal end of the housing and a beamsplitter;
  a separate electronic imaging device disposed at the proximal end of the housing, the electronic imaging device being aligned with the imaging assembly along the imaging axis;
  a microcontroller; and
  an illumination assembly including:
    a first light source for projecting light onto the beamsplitter and through the objective lens onto the eye of a patient as a focused spot, the first light source comprising an array of LEDs configured to produce an amber colored light, a second light source comprising an infrared light source, and a light detecting element, each of the second light source and the light detecting element being disposed distally of the objective lens and angled inwardly toward the imaging axis such that light emitted from the second light source and reflected from the eye of a subject can only be detected by the light detecting element when the ophthalmoscope is at a predetermined working distance and in which each of the electronic imaging device, the first light source and the light detecting element are coupled to the microcontroller wherein the array of LEDs and the separate electronic imaging device are not enabled by the microcontroller until the light detecting element produces a signal indicative that the predetermined working distance has been set and wherein the imaging assembly is configured to produce a 40 degree field of view of the eye of a patient.

2. The ophthalmoscope according to claim 1, wherein the light detecting element is a photodiode.

3. The ophthalmoscope according to claim 1, wherein the imaging assembly further includes a projection lens disposed proximally relative to the objective lens and the beamsplitter.

4. The ophthalmoscope according to claim 3 wherein the imaging assembly further includes a pair of relay lenses and a pair of imaging lenses proximally relative to the projection lens.

5. The ophthalmoscope according to claim 1, wherein the illumination assembly further includes an aperture mask relative to the array of LEDs along the illumination axis and in which the aperture mask includes a plurality of holes configured for alignment with each of the LEDs.

6. The ophthalmoscope according to claim 5, wherein the illumination assembly further includes a condenser lens disposed between the aperture mask and the beamsplitter.

7. An ophthalmoscope comprising:

an imaging assembly having a plurality of optical elements including an objective lens, a beamsplitter and a projection lens each aligned along an imaging axis, the beamsplitter being disposed proximally relative to the objective lens and the projection lens being disposed proximally relative to the beamsplitter;

a distance-setting light source that emits infrared light arranged in relation to a light detecting element, each of the distance-setting light source and the imaging assembly configured such that light emitted by the distance-setting light source is detected by the light detecting element only when the ophthalmoscope is set at a predetermined working distance relative to the eye of a patient;

a microcontroller;

a first electronic imaging device aligned along the imaging axis at a proximal end of the ophthalmoscope; and a second electronic imaging device disposed along an axis aligned with the beamsplitter, each of the first and second electronic imaging devices and the light detecting element being coupled to the microcontroller, the second electronic imaging device being configured to provide an advance viewing mode on a display of the first electronic imaging device wherein the microcontroller prevents the advance viewing mode until the ophthalmoscope has been set to the predetermined working distance and wherein the imaging assembly is configured to produce a 40 degree field of view of the eye of a patient.

8. The ophthalmoscope according to claim 7, wherein the second electronic imaging device is wirelessly connected to the microcontroller and the first electronic imaging device.

9. The ophthalmoscope according to claim 7, wherein the imaging assembly further includes relay lenses and imaging lenses disposed proximally from the projection lens along the imaging axis.

* * * * *